United States Patent
McCormick

Patent Number: 5,884,771
Date of Patent: Mar. 23, 1999

[54] DISPOSABLE HYGIENE CARRIER KIT

[76] Inventor: Diane L. McCormick, 425 County Rd. 19, Mound, Minn. 55364

[21] Appl. No.: 935,235

[22] Filed: Sep. 22, 1997

[51] Int. Cl.[6] .................................................. B65D 69/00
[52] U.S. Cl. .............................................. 206/581; 206/38
[58] Field of Search ............................. 206/38, 223, 440, 206/570, 581

[56] References Cited

U.S. PATENT DOCUMENTS

| | | |
|---|---|---|
| H1363 | 10/1994 | Leeker . |
| 1,056,218 | 3/1913 | Sahl . |
| 1,081,788 | 12/1913 | Terry . |
| 1,648,565 | 11/1927 | Primley ......................... 206/38 |
| 1,653,246 | 12/1927 | Zichy ........................... 206/223 |
| 2,124,920 | 7/1938 | Lambooy . |
| 2,143,062 | 1/1939 | Ericson et al. . |
| 2,478,412 | 8/1949 | McMahan ....................... 206/581 |
| 2,764,201 | 9/1956 | Whippo . |
| 2,843,170 | 7/1958 | Frankfurt . |
| 4,286,639 | 9/1981 | Murphy . |
| 4,702,378 | 10/1987 | Finkel et al. . |
| 4,848,588 | 7/1989 | Rasmussen . |
| 4,917,238 | 4/1990 | Schumacher ................... 206/223 |
| 4,960,208 | 10/1990 | Tempke ........................ 206/581 |
| 5,020,673 | 6/1991 | Adams . |
| 5,029,701 | 7/1991 | Roth et al. ................... 206/223 |
| 5,046,620 | 9/1991 | Barabino ...................... 206/581 |
| 5,261,531 | 11/1993 | Nieves . |
| 5,443,161 | 8/1995 | Jonese . |
| 5,579,916 | 12/1996 | Manko . |

FOREIGN PATENT DOCUMENTS 116914  12/1996  Switzerland ........................... 206/440

*Primary Examiner*—David T. Fidel
*Attorney, Agent, or Firm*—Nikolai, Mersereau & Dietz, P.A.

[57] ABSTRACT

A kit for use in disposing of spent medical supplies, contraceptive supplies, or feminine hygiene supplies includes an outer pouch, a plurality of inner pouches, a storage pouch, and a plurality of cleaning wipes. The outer pouch retains the remaining components of the kit. The inner pouches are used to individually contain spent supplies. The storage pouch is designed to segregate the used inner pouches and their contents from the remaining components of the kit. The wipes are used for general clean up. The kit allows for the discrete storage and disposal of the spent supplies.

6 Claims, 4 Drawing Sheets

DISPOSABLE HYGIENE CARRIER KIT

BACKGROUND OF THE INVENTION

1. Field of the Invention

The present invention relates to a compact and disposable kit containing a plurality of supplies used to collect and dispose of bodily fluids in a clean and discrete fashion. Depending upon the user's needs, such supplies can include feminine hygiene products, birth control products, ostomy products, incontinence products, or baby care products. Specifically, the present invention relates to a kit composed of an outer pouch or case for holding the remaining components of the kit as well as the supplies, a plurality of inner bags for holding used supplies, cleaning wipes or tissues, and a disposal pouch.

2. Description of the Prior Art

People value their privacy. People consider various medical situations private and try to avoid the perceived embarrassment arising from dealing with such situations in public. This is particularly true of many people who have had a colostomy or who suffer from incontinency. This is also true of women coping with menses.

A variety of hygiene products are available for collecting bodily fluids associated with various medical situations. Such items include sanitary napkins and tampons, ostomy products, condoms, sponges, as well as adult and infant diapers. People must carry such items while engaged in daily activities so such items are available when needed. People would generally prefer to be able to carry and dispose such items in a concealed and discrete fashion to avoid embarrassment.

Various kits and carrying cases have been developed over time to help people deal with such situations. For example, U.S. Pat. No. 5,443,161 dated Aug. 22, 1995 to David R. Jonese discloses a disposable baby changing kit. This kit includes an outer pouch specifically designed to contain (1) two diapers; (2) two moisture impermeable disposal bags; (3) two wet wiping elements; (4) baby powder; and (5) baby cream. Each of these items is intended to be used once before disposal. Soiled diapers and wiping elements can be placed in one of the two moisture impermeable disposal bags for future discarding.

U.S. Pat. No. 5,579,916 dated Dec. 3, 1996 to Katrina A. Manko discloses a feminine hygiene carrier kit. The kit includes a case made of a washable material having a plastic or similar lining. The kit is designed to contain two sanitary napkins, wiping products, and water impermeable bags for enclosing soiled hygiene articles for subsequent disposal.

U.S. Pat. No. 5,261,531 dated Nov. 16, 1993 to Felipe A. Nieves discloses an inexpensive feminine hygiene package and compact sanitary kit. The kit includes an outer container, a dry wipe, a wet wipe, and a sanitary napkin. The outer container can be used to dispose of the wipes and napkin after use.

None of the patents discussed above, taken separately or in combination, describe the instant invention as claimed. Nor do they disclose kits having all of the advantages of the instant invention.

SUMMARY OF THE INVENTION

The kit of the present invention provides for the convenient, discrete and inexpensive disposal of supplies used to collect bodily fluids. While the kit can be used with a variety of supplies such as ostomy products, incontinence products, birth control products, or the like, the kit will be described based upon its use with feminine hygiene products.

The kit contains four components: (1) an outer pouch; (2) a plurality of inner pouches; (3) one or more handling/cleaning wipes or tissues per inner pouch; and (4) a storage pouch. The outer pouch is designed to contain the remaining components of the kit and a supply of sanitary napkins, tampons, or both. The inner pouches are preferably made of a water resistant plastic or biodegradable material and can be sealed to enclose a used sanitary napkin or tampon. The handling/cleaning wipes can be of varying sizes. The storage pouch is designed to hold a plurality of inner pouches once they have been used to encapsulate a used sanitary product. The storage pouch includes a closure mechanism which permits it to be repeatedly and conveniently opened and closed. The storage pouch is particularly useful when engaged in extended activities, such as camping or boating, where there is no convenient and inconspicuous place to dispose of used sanitary products. It also helps segregate used from unused sanitary products.

Accordingly, it is a principal object of the invention to provide a kit having an outer pouch for carrying the remaining elements of the kit and possibly a supply of feminine hygiene products or the like.

Another object of the invention is to provide a kit having an outer pouch capable of discretely concealing its contents from view.

Another object of the invention is to provide a kit having an outer pouch which can be repeatedly and securely closed so that its contents will not inadvertently spill out.

Another object of the invention is to provide a kit having an outer pouch which is flexible and water resistant or biodegradable.

Still another object of the invention is to provide a kit having a plurality of inner pouches capable of holding used sanitary products or the like.

Another object of the invention is to provide a kit having a plurality of inner pouches which are capable of concealing their contents.

Another object of the invention is to provide a kit having a plurality of inner pouches which are sealable to prevent their contents from falling out.

A further object of the invention is to provide a kit having wipes that can be used to hold used sanitary products or the like when inserting such items into the inner pouches.

Another object of the invention is to provide a kit having wipes that can be used to clean up after changing sanitary products or the like.

A further object of the invention is to provide a kit having a storage pouch capable of holding a plurality of inner pouches and their contents.

Another object of the invention is to provide a storage pouch which is resealable so that items can be inserted into the pouch at varying times.

Another object of the invention is to provide a storage pouch which is inexpensive, disposable and capable of discretely segregating used and unused sanitary products.

These and other objects of the present invention will become readily apparent upon further review of the following specification and drawings.

DESCRIPTION OF THE PREFERRED EMBODIMENT

Figure 1:
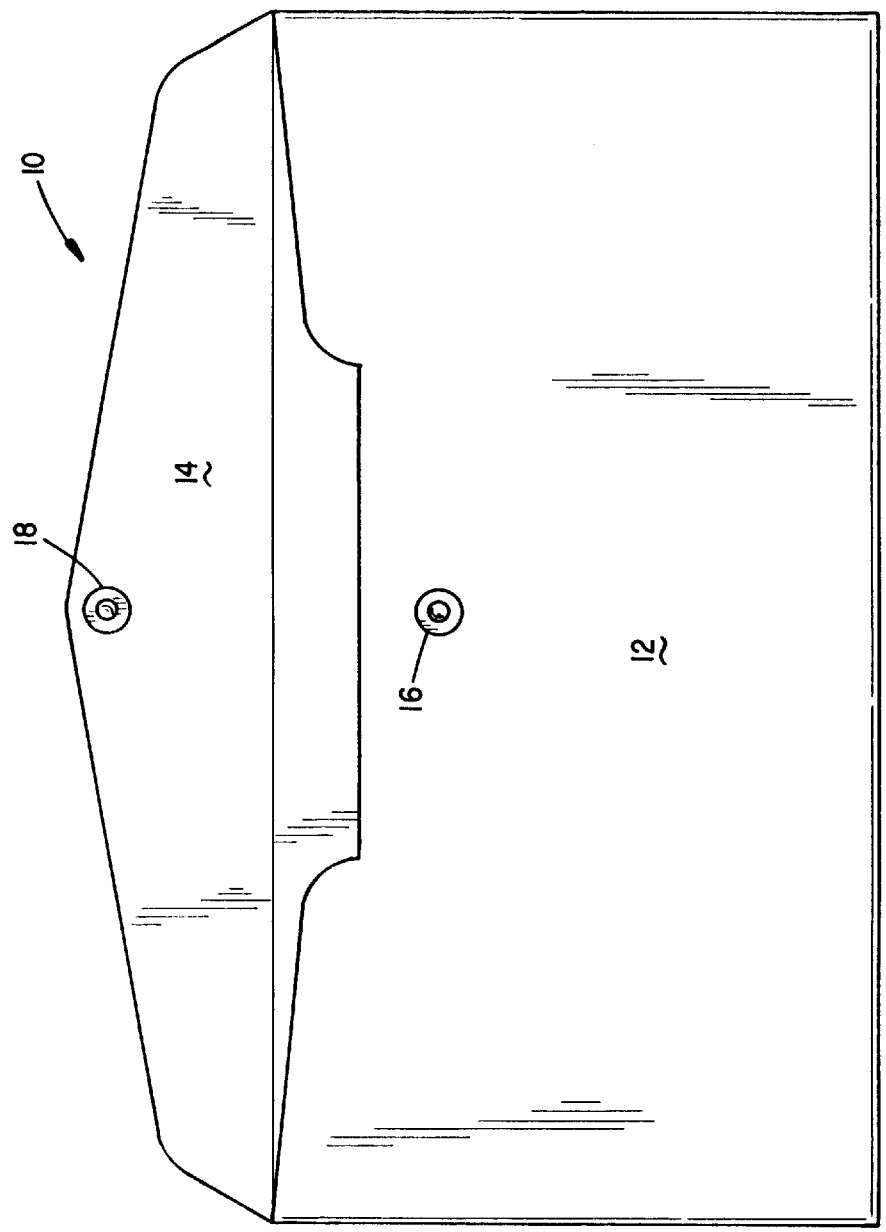
FIG. 1 is a front plan view of the outer pouch of the present invention.

As indicated above, the kit of the present invention can be used in conjunction with personal care supplies such as feminine hygiene products, birth control products, ostomy products, incontinence products, baby care products, or the like. The kit includes an outer pouch 10, a plurality of inner bags 20, cleaning wipes 30, and a storage and disposal pouch 40.

The outer pouch 10 is designed to contain the remaining components of the kit along with the supplies used with the kit. The outer pouch 10 preferably is resealable, opaque, and sturdy. The opaqueness of the pouch ensures that its contents cannot be casually observed from the exterior. The sturdiness and resealability of the pouch ensures that the contents are retained within the pouch and will not inadvertently spill out. The outer pouch 10 should also be flexible so that it can be folded or unfolded as needed. The outer pouch 10 will preferably be colored in an appropriate fashion so that it can be discretely used without undue attention.

The shape of the outer pouch 10 can vary. An envelope shape including a pocket 12, an opening 13, and a sealing flap 14 has proven to be acceptable. The outer pouch could also include a closure 16 on the pocket 12 and closure 18 on the flap 14. Closures 16 and 18 cooperate to releasably seal the flap 14 to the pocket 12, thereby closing the opening 13 to the pocket 12. Various suitable closures 16 and 18 are available. They could combine to form a hook and loop type closure, a snap type closure as shown, or a clasp type closure. Alternatively, an adhesive could be used so long as the adhesive provides a strong enough seal to retain the contents within the pouch 10 and yet permits one to repeatedly open and seal the flap 14 to the pocket 12 so that contents can be removed from or added to the pouch. Virtually any type of closure proven to be suitable for sealing a bag can be used including zippers, twist ties, interlocking mating strips, and the like.

The pouch 10 will also preferably be moisture resistant or biodegradable and inexpensive to make so that it can be considered disposable. Various plastic materials are available which can be used to create a pouch 10 having those essential characteristics identified above.

Figure 2:
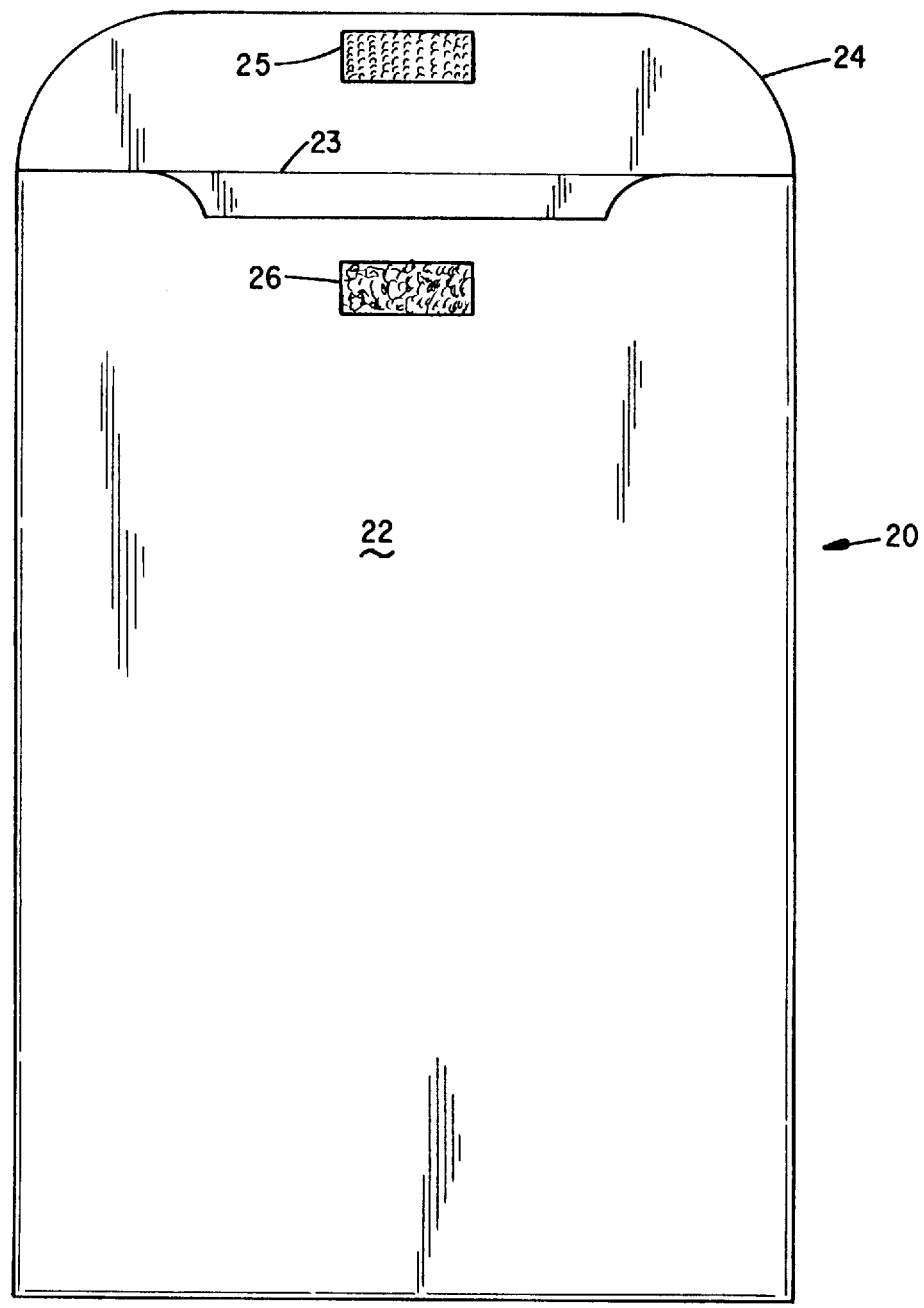
FIG. 2 is a front plan view of an inner pouch of the present invention.
Figure 3:
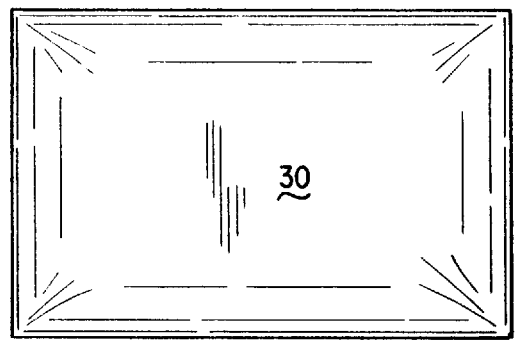
FIG. 3 is a plain view showing a wipe.
Figure 4:
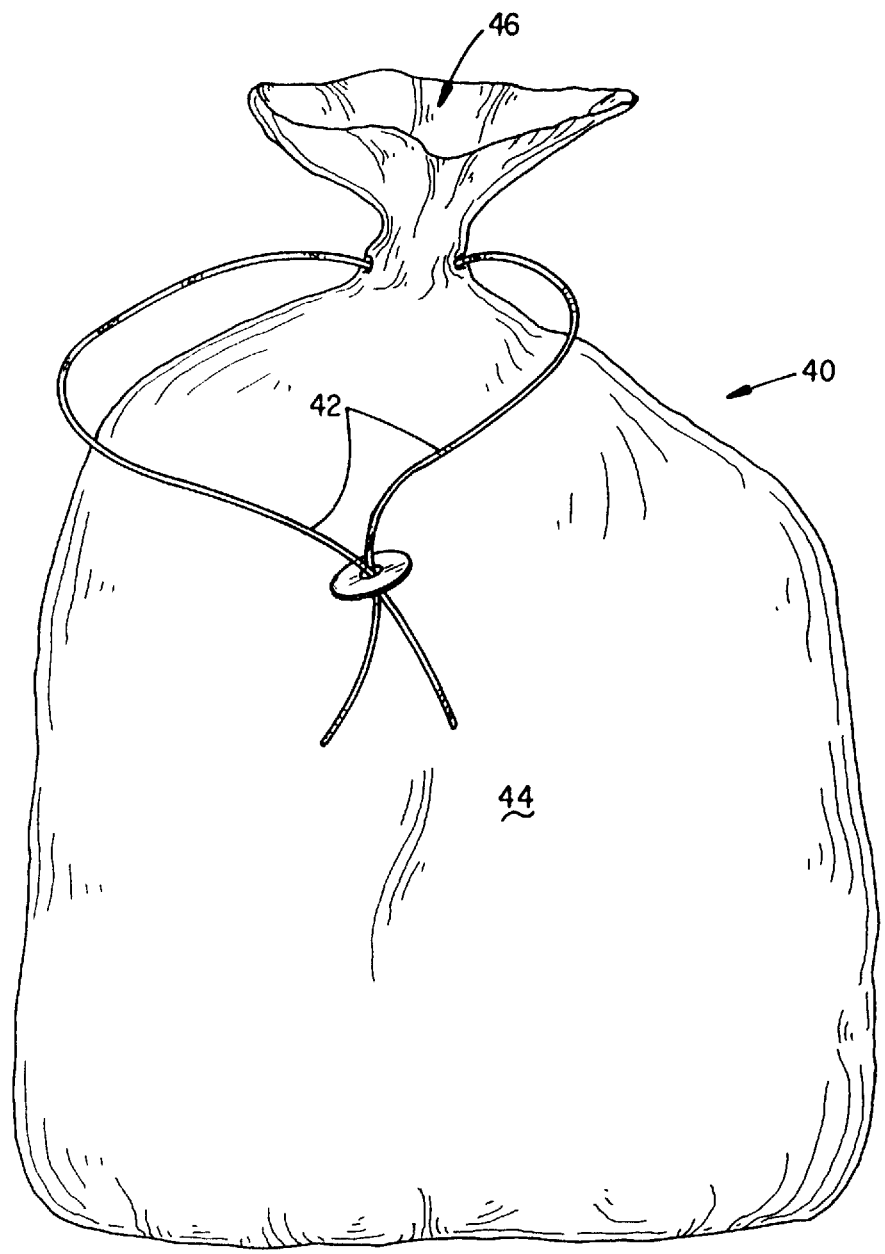
FIG. 4 is a perspective view of the storage pouch of the present invention.

The inner pouches 20 are preferably made of an opaque, sturdy, water resistant, plastic or biodegradable material. The inner pouches 20 include a pocket 22, an opening 23, and a flap 24. The flap 24 should be large enough so that it can be tucked in over the contents of the pocket 22 to seal the pouch 20. Alternatively, a closure arrangement, such as those described with respect to outer pouch 10, can be included to seal the pouches 20. FIG. 2 shows a hook and loop type closure consisting of a pad of hooks 25 and a pad of loops 26. The drawing is not intended, however to suggest that suitable closures are limited to hook and loop type closures. The size and shape of the inner pouches 20 will vary depending upon the used supplies to be deposited and enclosed therein. The various inner pouches 20 of a kit can also have different shapes and sizes. For example, when the kit is to be used with feminine hygiene products, some of the mixed inner pouches 20 can be sized to hold sanitary napkins or exclusively tampons or napkins and other inner pouches sized to hold tampons.

The cleaning wipes 30 can be of any of several well-known designs. For example, the wipes 30 can be in the form of a dry multi-ply tissue. The wipes 30 can also be in the form of a pre-moistened towelette. The wipes can generally be of any suitable size, shape, and configuration. The key is to provide wipes that can be used in handling used supplies and for cleanup after such use.

The storage pouch 40 is intended to hold one or more inner pouches 20 after the inner pouches 20 have been filled with a used supply and sealed. The form of the storage pouch 40 will, therefore, necessarily follow this function. Thus, the size and shape of the storage pouch 40 may vary depending upon the nature of the supplies being used. For example, a storage pouch 40 for tampons, condoms or sponges could be smaller than a storage pouch for ostomy products or diapers.

The storage pouch 40 must be sturdy. It is also preferably made from a flexible plastic material which is opaque and colored to conceal in an unobtrusive fashion the contents of the pouch 40. The pouch 40 should also be resealable. In the drawings, the pouch 40 is shown as including a pocket 44 having an opening 46. A draw string 42 is provided for closing the opening 46 of pocket 44. Other closure arrangements, including but not limited to those discussed above could also be used. The key is to provide a secure closure arrangement that permits the opening 46 of pocket 44 of storage pouch 40 to be readily and repeatedly opened and securely closed. The pouch 40, like all of the other components of the kit, should be inexpensive to produce so that it is considered disposable.

The availability of kits of the type contemplated by the present invention enables people to engage in a more active, less restrictive lifestyle. People visiting the homes of friends or relatives would prefer not to leave ostomy supplies, diapers, feminine hygiene products or the like behind when they depart. Also camping, climbing, boating, snowmobiling, and other outdoor activities can more readily be enjoyed if one need not have to worry about access to necessary supplies and the discrete disposal of same.

For example, a variety of hygiene articles have been developed for coping with the onset of menses. However, coping can still be difficult when camping in a remote setting. The outer pouch 10 of the present invention inconspicuously holds such supplies so that they are available for use. The inner pouches 20 allow used supplies to be individually stored and sealed after use. The wipes 30 allow for proper cleanup. Finally, the disposal pouch 40 allows the used supplies, after they are placed in the inner pouches 20, to be effectively, collectively and discretely segregated from unused feminine hygiene supplies and from other camping equipment and supplies. The disposal pouch 40 also allows the used feminine hygiene supplies to be quickly and discretely disposed of once a suitable waste receptacle is found.

The present invention may be embodied in other specific forms than those illustrated and discussed above without departing from the essential characteristics thereof. The illustrated embodiments are, therefore, to be considered in all respects as non-restrictive. The scope of the invention is intended to be defined by the appended claims rather than the description set forth above. All kits which come within the meaning of the claims, taken into account the proper range of equivalency, are intended to be covered by the claims.

What is claimed is:

1. A hygiene kit comprising an outer pouch, a plurality of inner pouches and a storage pouch:

(a) said outer pouch for holding said plurality of inner pouches and hygiene supplies, said outer pouch including a first storage pocket having a first open end, a first flap associated with the first open end movable between an open position which allows access to the interior of the first storage pocket through the first open end and a closed position in which the first flap prevents access to the interior of the pouch through the first open end and the contents of the pouch from spilling out of the first open end, and closure means which can be used to releasably secure said first flap in the closed position, said first pocket being made of an opaque material so that contents of the pocket cannot be viewed except through the first open end, said pocket and flap being made of a flexible, foldable and moisture resistant material;

(b) each of said plurality of inner pouches having a second pocket with a second open end and a second flap associated with the second open end and movable between an open position in which items can be inserted into the second pocket of the inner pouch and a closed position in which the second flap prevents access to the second pocket through the second open end and the contents from spilling out through the second open end, each of said inner pouch being made of a flexible, foldable, moisture resistant and biodegradable material, each of said inner pouches being sized to hold at least one hygiene supply after the hygiene supply has been used; and (c) said storage pouch including a third pocket having a third open end and means for closing said third open end, said third pocket being made of an opaque, foldable, flexible material and large enough to hold a plurality of the inner pouches and any hygiene supplies contained within said inner pouches.

2. The hygiene kit of claim 1 further including at least one cleaning wipe per inner pouch.

3. The hygiene kit of claim 1 wherein the closure means of the outer pouch is a hook and loop type closure.

4. The hygiene kit of claim 1 wherein the closure means of the outer pouch is a snap type closure.

5. The hygiene kit of claim 1 wherein the closure means of the outer pouch is a releasable adhesive patch.

6. The hygiene kit of claim 1 where the means for closing the third open end of the storage pouch is a draw string.

\* \* \* \* \*